United States Patent [19]

Grasselli et al.

[11] 4,397,771

[45] Aug. 9, 1983

[54] OXIDATION CATALYSTS

[75] Inventors: Robert K. Grasselli, Chagrin Falls; Dev D. Suresh, Warrensville Heights, both of Ohio

[73] Assignee: The Standard Oil Co., Cleveland, Ohio

[21] Appl. No.: 316,246

[22] Filed: Oct. 29, 1981

Related U.S. Application Data

[60] Continuation of Ser. No. 746,757, Dec. 2, 1976, abandoned, which is a division of Ser. No. 535,403, Jan. 13, 1975, abandoned.

[51] Int. Cl.$^3$ .................. B01J 23/16; B01J 21/02; B01J 27/14; B01J 27/02
[52] U.S. Cl. .................. 252/467; 252/432; 252/435; 252/437; 252/439; 252/462; 252/465; 252/468; 252/469
[58] Field of Search ............... 252/432, 435, 437, 439, 252/462, 465, 467, 468, 469

[56] References Cited

U.S. PATENT DOCUMENTS

| | | | |
|---|---|---|---|
| 3,179,694 | 4/1965 | Eygen et al. ................ 252/469 X |
| 3,342,849 | 9/1967 | Brill et al. ................ 260/465.3 |
| 3,345,397 | 10/1967 | Finley ................ 252/467 X |
| 3,347,899 | 10/1967 | Coporali et al. ................ 260/465.3 |
| 3,642,930 | 2/1972 | Grasselli et al. ................ 252/437 X |
| 3,801,670 | 4/1974 | Shiraish et al. ................ 252/437 X |
| 3,872,148 | 3/1975 | Umemura et al. ................ 252/468 X |
| 3,875,220 | 4/1975 | White et al. ................ 252/469 X |
| 3,892,794 | 7/1975 | Grasselli et al. ................ 260/465.3 |
| 3,956,181 | 5/1976 | Grasselli et al. ................ 252/470 X |
| 4,001,317 | 1/1977 | Grasselli et al. ................ 260/604 R X |
| 4,052,450 | 10/1977 | Krabetz et al. ................ 252/432 |

Primary Examiner—Delbert E. Gantz
Assistant Examiner—William G. Wright
Attorney, Agent, or Firm—J. E. Miller, Jr.; H. D. Knudsen; L. W. Evans

[57] ABSTRACT

The invention is an oxidation catalyst which contains at least a Group IIA or Group IIB element or manganese plus as required elements, chromium, bismuth and molybdenum. The catalysts can optionally contain a number of other elements and are useful for various oxidation reactions, especially the ammoxidation of propylene or isobutylene to obtain acrylonitrile or methacrylonitrile, the oxidation of propylene or isobutylene to obtain acrolein or methacrolein and the oxidative dehydrogenation of olefins containing 4 or 5 carbon atoms to obtain the corresponding diolefin.

7 Claims, No Drawings

OXIDATION CATALYSTS

This is a continuation of application Ser. No. 746,757 filed Dec. 2, 1976, now abandoned which is a Divisional of Ser. No. 535,403 filed Jan. 13, 1975, now abandoned.

BACKGROUND OF THE INVENTION

Oxidation catalysts similar to those of the invention are known although the catalysts of the invention have a different composition from any of the catalysts in the art. The catalysts of the invention are prepared according to techniques that are generally applicable to the catalysts of the art.

The oxidation reactions in which these catalysts are especially suitable are well known. Broadly, these reactions are a vapor phase reaction using the solid catalyst of the invention. The reactants are passed over the catalyst in the presence of molecular oxygen at an elevated temperature to obtain the desired product.

SUMMARY OF THE INVENTION

This invention is new oxidation catalysts of the formula $$A_a\ C_c\ D_d\ Cr_e\ Bi_f Mo_{12}\ O_x$$

wherein

A is an alkali metal, Tl, In, Ag, Cu, Sn, W, Rare earth metal or mixture thereof:

C is a Group IIA or Group IIB element, manganese or mixture thereof;

D is Ni, Co, P, As, Sb, Ge, B, or mixture thereof;

and wherein a is 0-4;

c is 0.5 to 20;

d is 0-2;

e and f are 0.1-12 and x is the number of oxygens required to satisfy the valence requirements of the other elements present.

These oxidation catalysts are useful for a number of oxidation reactions described below.

The catalysts covered by the present invention are any of those that are delimited by the formula above. Of special interest in the invention are those catalysts which contain calcium, magnesium, manganese, cadmium, zinc or mixture thereof. This is accomplished in the formula set forth above by setting C equal to these recited elements. Also of particular interest in the invention are those catalysts that contain potassium, copper, tin or mixture thereof. This is accomplished in the formular setting A equal to these elements and providing that a is greater than zero.

The catalysts of the invention are prepared in a manner which is similar to the preparations conducted in the art for related catalysts. See for example, U.S. Pat. No. 3,642,930. Normally, the catalysts are prepared by coprecipitation of soluble salts from an aqueous solution. The precipitate is then dried and heat treated in air to form a catalytic oxide structure.

In the formula describing the catalysts of the invention, it is seen that the number of oxygens is designated by "x". This x is of variable nature because in actual operation of these oxidation catalysts, the catalysts are continually gaining and losing oxygen, and the setting of a strict number on these catalysts accordingly would be an imprecise statement. Broadly, the value ascribed to x would fall within the range of the number of oxygens required in the highest oxidation state to evalue greater than 50% of that number of oxygenation to signify the reduced state.

Although the reactions in which these catalysts are especially suitable are know in the art, the following discussion gives some broad parameters in which the reactions are normally conducted. For the ammoxidation of propylene and isobutylene, the reaction is conducted in the presence of a catalyst described above at a temperature of about 200° to about 600° C. The contact time may range from less than a second to 20 seconds or more. The reaction can be conducted with the catalyst of the invention either in a fixed bed form or a fluid bed form at atmospheric, subatmospheric or superatmospheric pressure.

The other reactions for which these catalysts are especially useful, the oxidation of other olefins, are well known in the art and the parameters applied to the ammoxidation reaction would apply also to these reactions.

SPECIFIC EMBODIMENTS

Examples 1-10 - Preparation of various catalysts.

Various catalysts consisting of 80% of the active material and 20% of silica were prepared as described below.

Example 1

80% $K_{0.1}Mg_7Cr_3BiP_{0.5}Mo_{12}O_x$ and 20% $SiO_2$

A slurry consisting of water and 63.56 g. $(NH_4)_6Mo_7O_{24}.4H_2O$; 48.37 g. Nalco, 40% silica sol; and 3.46 g. $H_3PO_4$, 42.5% solution; was prepared and combined with a solution of 9.00 g. $CrO_3$; 53.85 g. g. $Mg(NO_3)_2.6H_2O$; 3.03 g. $KNO_3$, 10% solution; and 14.55 g. $Bi(NO_3)_3.5H_2O$. The slurry was evaporated to dryness and the resulting solid was further dried overnight at 120° C. The solid was then heated in air at 290° C. for three hours, 425° C. for three hours and at 550° C. for 16 hours to form the active catalytic complex.

Example 2

80% $K_{0.1}Mg_{7.5}Ni_{0.5}Cr_3BiP_{0.5}Mo_{12}O_x$ and 20% $SiO_2$

This catalyst was prepared in the same manner as described above using a slurry containing 63.56 g. $(NH_4)_6Mo_7P_{24}.4H_2O$; 49.50 g. Nalco, 40% silica sol; and 3.46 g. of a 42.5% solution of $H_3PO_4$; and a solution containing 22.24 g. $Cr(C_2H_3O_2)_3.H_2O$; 57.70 g. $Mg(NO_3)_2.6H_2O$; 4.36 g. $Ni(NO_3)_2.6H_2O$; 3.03 g. of a 10% solution of $KNO_3$; and 14.55 g. $Bi(NO_3)_3.5H_2O$. The solid separated was heat treated in the manner described above.

Example 3

80% $K_{0.1}Mn_7Cr_3BiP_{0.5}Mo_{12}O_x$ and 20% $SiO_2$

This catalyst was prepared in the same manner as described in Example 1 using a slurry containing 63.56 g. $(NH_4)_6Mo_7O_{24}.4H_2O$; 52.42 g. Nalco, 40% silica sol; and 3.46 g. $H_3PO_4$, 42.5% solution; and a solution containing 9.00 g. $CrO_3$; 75.18 g. $Mn(NO_3)_2$, 50% solution; 3.03 g. $KNO_3$, 10% solution; and 14.55 g. $Bi(NO_3)_3.5-H_2O$. The solid separated was heat treated in the manner described above.

Example 4

80% $K_{0.1}Ni_{0.5}Mn_{6.5}Cr_3BiP_{0.5}Mo_{12}O_x$ and 20% $SiO_2$

This catalyst was prepared in the same manner as described in Example 1 using a slurry containing 63.56 g. $(NH_4)_6Mo_7O_{24}.4H_2O$; 51.13 g. Nalco, 40% $SiO_2$; and 3.46 g. $H_3PO_4$, 42.5% solution; and a solution containing 9.00 g. $CrO_3$; 69.79 g. $Mn(NO_3)_2$, 50% solution; 4.36 g. $Ni(NO_3)_2.6H_2O$; 14.55 g. $Bi(NO_3)_3.5H_2O$; and 3.03 g. $KNO_3$. The solid separated was heat treated in the manner described above.

Example 5

80% $K_{0.8}Mg_{3.5}Mn_{3.5}Cr_3BiP_{0.5}Mo_{12}O_x$ and 20% $SiO_2$

This catalyst was prepared in the same manner as described in Example 1 using a slurry containing 63.56 g. $(NH_4)_6Mo_7O_{24}.4H_2O$; 50.43 g. Nalco, 40% silica sol; and 3.46 g. $H_3PO_4$, 42.5% solution; and a solution containing 9.00 g. $CrO_3$; 26.92 g. $Mg(NO_3)_2.6H_2O$; 37.60 g. $Mn(NO_3)_2$, 50% solution; 3.03 g. of 45% KOH solution; and 14.55 g. $Bi(NO_3)_3.5H_2O$. The solid separated was heat treated in the manner described above.

Example 6

80% $Cs_{0.1}Co_{0.5}Mg_{6.5}Cr_3BiSb_{0.5}Mo_{12}O_x$ and 20% $SiO_2$

This catalyst was prepared in the same manner described above using a slurry containing 63.56 g. $(NH_4)_6Mo_7O_{24}.4H_2O$; 48.28 g. Nalco, 40% $SiO_2$; 2.19 g. $Sb_2O_3$; and a solution containing 9.00 g. $CrO_3$; 50.00 g. $Mg(NO_3)_2.6H_2O$; 4.37 g. $Co(NO_3)_2.6H_2O$; 14.55 g. $Bi(NO_3)_3.5H_2O$; and 0.58 g. $CsNO_3$. The solid separated was heat treated in the manner described above.

Example 7

80% $Mg_7Cr_{1.5}Cu_{1.5}BiP_{0.5}Mo_{12}O_x$ and 20% $SiO_2$

This catalyst was prepared in the same manner described above using a slurry containing 63.56 g. $(NH_4)_6Mo_7O_{24}.4H_2O$; 47.78 g. Nalco, 40% silica sol; and 3.46 g. $H_3PO_4$, 42.5% solution; and a solution containing 53.83 g. $Mg(NO_3)_2.6H_2O$; 10.88 g. $Cu(NO_3)_2.3H_2O$; 4.50 g. $CrO_3$; and 14.55 g. $Bi(NO_3)_3.5H_2O$. The solid separated was heat treated in the manner described above.

Example 8

80% $Mg_7Cr_{1.5}Sn_{1.5}BiP_{0.5}Mo_{12}O_x$ and 20% $SiO_2$

This catalyst was prepared in the same manner described above using a slurry containing 63.56 g. $(NH_4)_6Mo_7O_{24}.4H_2O$; 49.78 g. Nalco, 40% silica sol; and 3.46 g. of a 42.5% solution of $H_3PO_4$; and a solution containing 53.83 g. $Mg(NO_3)_2.6H_2O$; 14.55 g. $Bi(NO_3)_3.5H_2O$; 4.50 g. $CrO_3$; and 6.78 g. $SnO_2$. The solid separated was heat treated in the manner described above.

Example 9

80% $Ca_1Cr_{0.5}Sn_{0.5}Bi_{0.2}Mo_2O_x$ and 20% $SiO_2$

This catalyst was prepared in the same manner described above using a slurry containing 22.95 g. $(NH_4)_6Mo_7O_{24}.4H_2O$, 21.09 g. Nalco, 40% silica sol; and a solution containing 15.35 g. $Ca(NO_3)_2.4H_2O$; 3.25 g. $CrO_3$; 6.31 g. $Bi(NO_3)_3.5H_2O$; and 4.90 g. $SnO_2$. The solid separated was heat treated in the manner described above.

Example 10

80% $K_{0.5}Cd_{3.5}Mg_{3.5}Cr_3BiP_{0.5}Mo_{12}O_x$ and 20% $SiO_2$

This catalyst was prepared in the same manner described above using a slurry containing 63.56 g. $(NH_4)_6Mo_7O_{24}.4H_2O$; 53.20 g. Nalco, 40% $SiO_2$; and 3.46 g. of a 42.5% solution of $H_3PO_4$; and a solution containing 9.00 g. $CrO_3$; 14.55 g. $Bi(NO_3)_3.5H_2O$; 32.39 g. $Cd(NO_3)_2.4H_2O$; 26.92 g. $Mg(NO_3)_2.6H_2O$; and 1.52 g. $KNO_3$. The solid separated was heat treated in the manner described above.

Example 10-a

80% $K_{1.5}Zn_3Ni_{0.5}Cr_3Bi_3P_{0.5}Mo_{12}O_x$ and 20% $SiO_2$

This catalyst was prepared in the same manner described above using a slurry containing 63.56 g. $(NH_4)_6Mo_7O_{24}.4H_2O$; 57.03 g. Nalco, 40% $SiO_2$; and 3.46 g. of a 42.5% solution of $H_3PO_4$; and a solution containing 9.00 g. $CrO_3$; 43.65 g. $Bi(NO_3)_3.5H_2O$; 7.32 g. ZnO, 4.36 g. $Ni(NO_3)_2.6H_2O$; and 4.55 g. $KNO_3$. The slurry was evaporated to dryness and heat treated in the manner described above.

Example 11 - Preparation of a catalyst without silica.

The preparation of a catalyst of $Ca_2Sn_{0.5}Cr_{0.5}BiMo_2O_x$ was attempted as follows.

In 20 cc. of water 24.93 g. of $Ca(NO_3)_2.4H_2O$ was dissolved and 2.65 g. $CrO_3$ and 3.99 g. $SnO_2$ were added. To this mixture was added dropwise a solution of 18.72 g. $(NH_4)_6Mo_7O_{24}.4H_2O$ dissolved in 50 cc. of a 9.3% ammonia solution, and then 25.36 g. $Bi(NO_3)_3.5H_2O$ dissolved in 40 cc. of a 13.8% $HNO_3$ solution was added. The pH of the mixture was brought to 4.0–4.5 with about 10 cc. of ammonium hydroxide. The mixture was stirred for 30 minutes and aged for 48 hours. The catalyst was washed with 1440 ml of water, filtered and dried at 120° C. The catalyst was heat treated at 540° C. for 16 hours. Due to the leaching of calcium during the washing, the final composition of the catalyst was determined to be $Ca_{1.8}Sn_3Cr_3Bi_6Mo_{12}O_x$.

Examples 12–30 - Preparation of acrylonitrile.

The catalysts employed in Examples 1–10 were tested in the ammoxidation of propylene. The feed employed had a ratio of propylene/ammonia/air/steam of 1/1.1/10/4. The catalyst in each of the reactions was ground and screened and charged to the 5 cc. reaction zone of a tubular reactor constructed of a 1 cm. inside diameter stainless steel tube. Table 1 shows the catalyst employed and the reaction temperature and contact time and the results used with the catalysts. The results are expressed in the following terms:

$$\% \text{ conversion} = \frac{\text{amount of reactant reacted} \times 100}{\text{amount of reactant fed}}$$

$$\% \text{ selectivity} = \frac{\text{amount of product formed} \times 100}{\text{amount of reactant reacted}}$$

$$\% \text{ single pass yield} = \frac{\text{amount of product formed} \times 100}{\text{amount of reactant fed}}$$

TABLE 1

Ammoxidation of Propylene

| Example | Catalyst | C.T. Sec. | Temp. °C. | Single Pass Yield | Conversion | Selectivity |
|---|---|---|---|---|---|---|
| 12 | $K_{0.1}Mg_7Cr_3BiP_{0.5}Mo_{12}O_x$ | 6 | 480 | 52.7 | 85.6 | 62 |
| 13 | $K_{0.1}Mg_7Cr_3BiP_{0.5}Mo_{12}O_x$ | " | 460 | 58.7 | 75.0 | 78 |
| 14 | $K_{0.1}Mg_7Cr_3BiP_{0.5}Mo_{12}O_x$ | 3 | " | 46.5 | 59.2 | 79 |
| 15 | $K_{0.1}Mg_{7.5}Ni_{0.5}Cr_3BiP_{0.5}Mo_{12}O_x$ | 6 | 480 | 74.0 | 99.3 | 75 |
| 16 | $K_{0.1}Mg_{7.5}Ni_{0.5}Cr_3BiP_{0.5}Mo_{12}O_x$ | 3 | " | 71.2 | 88.3 | 81 |
| 17 | $K_{0.1}Mn_7Cr_3BiP_{0.5}Mo_{12}O_x$ | " | 500 | 27.3 | 42.2 | 65 |
| 18 | $K_{0.1}Mn_7Cr_3BiP_{0.5}Mo_{12}O_x$ | " | 460 | 26.1 | 29.1 | 87 |
| 19 | $K_{0.1}Mn_{6.5}Ni_{0.5}Cr_3BiP_{0.5}Mo_{12}O_x$ | 6 | 480 | 40.7 | 75.8 | 54 |
| 20 | $K_{0.8}Mg_{3.5}Mn_{3.5}Cr_3BiP_{0.5}Mo_{12}O_x$ | " | 500 | 71.7 | 85.1 | 84 |
| 21 | $K_{0.8}Mg_{3.5}Mn_{3.5}Cr_3BiP_{0.5}Mo_{12}O_x$ | 3 | 480 | 56.5 | 68.0 | 83 |
| 22 | $Cs_{0.1}Mg_{6.5}Co_{0.5}Cr_3BiSb_{0.5}Mo_{12}O_x$ | 6 | 480 | 31.1 | 47.2 | 66 |
| 23 | $Mg_7Cr_{1.5}Cu_{1.5}BiP_{0.5}Mo_{12}O_x$ | 11 | 460 | 54.7 | 87.8 | 59 |
| 24 | $Mg_7Cr_{1.5}Cu_{1.5}BiP_{0.5}Mo_{12}O_x$ | " | 430 | 42.2 | 74.1 | 57 |
| 25 | $Mg_7Cr_{1.5}Cu_{1.5}BiP_{0.5}Mo_{12}O_x$ | " | 420 | 32.8 | 66.1 | 49 |
| 26 | $Mg_7Cr_{1.5}Sn_{1.5}BiP_{0.5}Mo_{12}O_x$ | 6 | 460 | 64.8 | 96.7 | 67 |
| 27 | $Mg_7Cr_{1.5}Sn_{1.5}BiP_{0.5}Mo_{12}O_x$ | 3 | " | 65.3 | 87.6 | 75 |
| 28 | $Ca_6Cr_3Sn_3Bi_{1.2}Mo_{12}O_x$ | 6 | " | 50.9 | 83.4 | 61 |
| 29 | $Ca_6Cr_3Sn_3Bi_{1.2}Mo_{12}O_x$ | 3 | 460 | 55.1 | 78.4 | 70 |
| 30 | $Ca_6Cr_3Sn_3Bi_{1.2}Mo_{12}O_x$ | " | 440 | 56.0 | 74.2 | 74 |

Example 31 - Preparation of acrylonitrile using a 100% active catalyst.

The catalyst prepared in Example 10 was used in the production of acrylonitrile using a different reactant feed of propylene/ammonia/air/steam in the ratio of 1/1/8/2. The temperature of 450° C. and apparent contact time of three seconds were used. This reaction gave a 68.4% single pass yield to acrylonitrile at a 79% selectivity.

Examples 32-36 - Ammoxidation of isobutylene.

Various catalysts prepared above were tested in the ammoxidation of isobutylene using a contact time of 3 seconds and a reactant feed of isobutylene/ammonia/air/steam of 1/1.1/10/4. The results of these experiments are shown in Table 2.

TABLE 2

Ammoxidation of Isobutylene

| Example | Catalyst | Temp. °C. | Single Pass Yield | Conversion | Selectivity |
|---|---|---|---|---|---|
| 32 | $K_{0.8}Mg_{3.5}Mn_{3.5}Cr_3BiP_{0.5}Mo_{12}O_x$ | 460 | 71.8 | 98.6 | 73 |
| 33 | $Cs_{0.1}Co_{0.5}Mg_{6.5}Cr_3BiSb_{0.5}Mo_{12}O_x$ | 450 | 64.1 | 94.1 | 68 |
| 34 | $K_{0.1}Mg_{7.5}Ni_{0.5}Cr_3BiP_{0.5}Mo_{12}O_x$ | 440 | 64.1 | 95.3 | 67 |
| 35 | $K_{0.5}Cd_{3.5}Mg_{3.5}Cr_3BiP_{0.5}Mo_{12}O_x$ | 460 | 70.5 | 100 | 71 |
| 36* | $K_{1.5}Zn_3Ni_{0.5}Cr_3Bi_3P_{0.5}Mo_{12}O_x$ | " | 77.4 | 96.6 | 80 |

*Contact time 6 seconds; feed composition, isobutylene/ammonia/air/steam = 1/2/15/4

Example 37 - Oxydehydrogenation of butene-1.

The catalyst of Example 2 was employed in the oxydehydrogenation of butene-1 using a ratio of butene-1/air of 1/14. The reaction was conducted at 400° C. using a contact time of 3 seconds. The single pass yield to butadiene was 77.6%, the conversion of the butene-1 was 86.9% and the selectivity to butadiene was 90%.

Example 38 - Oxydehydrogenation of butene -2.

Using the catalyst of Example 5, butane-2 was converted to butadiene using a reactant ratio of cis/trans butene-2 (42.5% cis+57.5% trans)/air of 1/11. A reaction temperature of 490° C. and an apparent contact time of 3 seconds were used. The single pass yield to butadiene was 68.1%. The conversion of butene-2 was 73.1% and the selectivity was 93%.

In the same manner as shown above, other catalysts within the scope of the formula may be prepared and used in ammoxidation, oxydehydrogenation and oxidation reactions.

We claim:

1. An oxidation catalyst having the formula
$$A_aC_cD_dCr_eBi_fMo_{12}O_x$$
wherein
A is an alkali metal Tl, Ag, Cu, Sn, W or mixtures thereof, wherein A contains at least alkali metal;
C is a Group IIA or Group IIB element, manganese or mixture thereof;
D is Ni, Co, P, As, Sb, Ge, B, or mixture thereof;
and wherein
a is 0-4;
c is 0.5 to 20;
d is 0-2;
e and f are 0.1-12, and
x is a number of oxygens required to satisfy the valence requirements of the other elements present.
said catalyst being free of indium, gallium, aluminum and rare earth metals.

2. The oxidation catalyst of claim 1 wherein C is calcium, magnesium, manganese, cadmium, zinc or mixture thereof.

3. The oxidation catalyst of claim 1 wherein A is potassium, copper, tin or mixture thereof and a is greater than zero.

4. The catalyst of claim 1 wherein C is Mn.

5. The catalyst of claim 1 wherein C is a Group IIB element, Mn or a mixture thereof.

6. The catalyst of claim 1 wherein C is Mn.

7. An oxidation catalyst having the formula $$A_a C_c D_d Cr_e Bi_f Mo_{12} O_x$$

wherein

A is an alkali metal Tl, Ag, Cu, Sn, W, rare earth metal or mixtures thereof, wherein A contains at least alkali metal;

C is a Group IIB element;

D is Ni, Co, P, As, Sb, Ge, B, or mixture thereof;

and wherein a is 0–4;

c is 0.5 to 20;

d is 0–2;

e and f are 0.1–12, and x is the number of oxygens required to satisfy the valence requirements of the other elements present.

* * * * *